US008435170B2

(12) United States Patent
Wood et al.

(10) Patent No.: US 8,435,170 B2
(45) Date of Patent: May 7, 2013

(54) POSITIONING SYSTEM FOR SECURING A TREATMENT INSTRUMENT AT THE END OF A MEDICAL DEVICE

(75) Inventors: Mark Wood, Shrewsbury, MA (US); John Hutchins, North Attleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1104 days.

(21) Appl. No.: 12/314,500

(22) Filed: Dec. 11, 2008

(65) Prior Publication Data

US 2009/0182194 A1 Jul. 16, 2009

Related U.S. Application Data

(60) Provisional application No. 61/006,416, filed on Jan. 11, 2008.

(51) Int. Cl.
*A61B 1/00* (2006.01)

(52) U.S. Cl.
USPC ........... 600/107; 600/104; 600/106; 600/127; 600/129

(58) Field of Classification Search ................. 600/104, 600/106–107, 127, 129, 153
See application file for complete search history.

(56) References Cited

U.S. PATENT DOCUMENTS

| 4,436,087 | A | * | 3/1984 | Ouchi | 600/106 |
|---|---|---|---|---|---|
| 4,452,236 | A | * | 6/1984 | Utsugi | 600/107 |
| 4,593,680 | A | * | 6/1986 | Kubokawa | 600/107 |
| 5,343,853 | A | * | 9/1994 | Komi | 600/107 |
| 5,460,168 | A | * | 10/1995 | Masubuchi et al. | 600/123 |
| 5,569,157 | A | * | 10/1996 | Nakazawa et al. | 600/107 |
| 5,855,569 | A | * | 1/1999 | Komi | 604/526 |
| 7,087,010 | B2 | * | 8/2006 | Ootawara et al. | 600/104 |
| 7,691,055 | B2 | * | 4/2010 | Carter et al. | 600/107 |
| 8,066,631 | B2 | * | 11/2011 | Wimmer | 600/107 |
| 2006/0235271 | A1 | * | 10/2006 | Carter et al. | 600/107 |

* cited by examiner

*Primary Examiner* — Matthew J Kasztejna
(74) *Attorney, Agent, or Firm* — Bookoff McAndrews, PLLC

(57) ABSTRACT

Embodiments of the invention include a medical device for accessing a patient's body portion and used for diagnosis and treatment of medical conditions. Embodiments of the invention may include a particular endoscopic positioning mechanism for placing an endoscope and an additional treatment device within desired body portions in order to assist in diagnosis and treatment of anatomical diseases and disorders. In particular, a medical device according to an embodiment of the invention includes a positioning mechanism configured to maintain the relative position of a treatment instrument with respect to an underlying endoscope during a treatment procedure.

13 Claims, 12 Drawing Sheets

POSITIONING SYSTEM FOR SECURING A TREATMENT INSTRUMENT AT THE END OF A MEDICAL DEVICE

CLAIM FOR PRIORITY

This patent application claims the benefit of U.S. Provisional Application No. 61/006,416, filed Jan. 11, 2008, which is incorporated herein by reference in its entirety.

FIELD OF THE INVENTION

The invention relates to an endoscope system for accessing a patient's body portion and used for diagnosis and treatment of medical conditions. For example, embodiments of the invention may include a particular endoscopic positioning mechanism for placing an endoscope and an additional treatment device within desired body portions in order to assist in diagnosis and treatment of anatomical diseases and disorders.

BACKGROUND OF THE INVENTION

Endoscopes for medical use have been adopted for various diagnostic and medical treatment procedures. Endoscopes have been used for the diagnosis and treatment of a wide range of diseases and disorders that often require a physician to access the tortuous and relatively small cross-sectional areas of a patient's internal anatomical body lumens. A patient's pancreaticobiliary system (including the anatomical regions of the gall bladder, pancreas, and the biliary tree), for example, is accessed for diagnosis, and/or treatment of disorders of certain portions of the digestive system.

During treatment of the digestive system, endoscopes are often used to access and visualize a patient's pancreaticobiliary system. Once the endoscope is positioned in the desired body portion, a treatment instrument can be advanced through the working channel of the endoscope to the desired body portion. The endoscope and treatment instrument may then be manipulated as desired for visualization and treatment respectively.

Endoscopic retrograde cholangiopancreatography (ERCP) is one example of a medical procedure that uses an endoscope. ERCP can enable the physician to diagnose problems in the liver, gallbladder, bile ducts, and pancreas. The liver is a large organ that, among other things, makes a liquid called bile that helps with digestion. The gallbladder is a small, pear-shaped organ that stores bile until it is needed for digestion. The bile ducts are tubes that carry bile from the liver to the gallbladder and small intestine. These ducts are sometimes called the biliary tree. The pancreas is a large gland that produces chemicals that help with digestion and hormones such as insulin.

The biliary system delivers bile produced by the liver to the duodenum where the bile assists other gastric fluids in digesting food. The biliary system includes the liver, as well as a plurality of bodily channels and organs that are disposed between the liver and the duodenum. Within the liver lobules, there are many fine "bile canals" that receive secretions from the hepatic cells. The canals of neighboring lobules unite to form larger ducts, and these converge to become the "hepatic ducts." They merge, in turn, to form the "common hepatic duct." The "common bile duct" is formed by the union of the common hepatic and the cystic ducts. It leads to the duodenum, where its exit is guarded by a sphincter muscle. This sphincter normally remains contracted until the bile is needed, so that bile collects in the common bile duct and backs up to the cystic duct. When this happens, the bile flows into the gallbladder and is stored there.

ERCP is used primarily to diagnose and treat conditions of the bile ducts, including gallstones, inflammatory strictures (scars), leaks (from trauma and surgery), and cancer. ERCP combines the use of x-rays and an endoscope. Through the endoscope, the physician can see the inside of the stomach and duodenum, and inject dyes into the ducts in the biliary tree and pancreas so they can be seen on x-rays.

An ERCP is performed primarily to identify and/or correct a problem in the bile ducts or pancreas. For example, if a gallstone is found during the exam, it can often be removed by means of a treatment instrument, eliminating the need for major surgery. If a blockage in the bile duct causes yellow jaundice or pain, it can be relieved through the use of a treatment instrument inserted through the endoscope.

Since endoscopes are often used to access the tortuous and relatively small cross-sectional areas of a patient's internal anatomical body lumens, repeated manipulation and positioning of an endoscope during a medical procedure can cause problematic side-effects. For example, repeated manipulation and positioning of the endoscope can cause unnecessary trauma to a patient's internal tissues. Improper placement and repeated attempts to access a desired treatment region can exacerbate tissue trauma as well as unnecessarily prolong the medical procedure. Some existing endoscope devices include mechanical positioning components (e.g., elevators) used to manipulate treatment instruments inserted within a working channel of an endoscope. Such positioning devices suffer from imprecise force transmission and slippage between moving components. Accordingly, there is a need for more precise endoscope manipulation as well as manipulating an underlying treatment instrument through an access channel of an endoscope.

Thus, it is desirable to have an endoscope assembly that can more precisely access the tortuous and relatively small cross-sectional areas of certain anatomical body lumens, and more precisely manipulate a treatment device provided within an access channel of an endoscope.

SUMMARY OF THE INVENTION

Embodiments of the present invention are directed to an improved endoscope system and a positioning device for manipulating a treatment device that obviates one or more of the limitations and disadvantages of prior medical devices.

In one embodiment, a medical device comprises an elongated flexible tube including a distal end and a proximal end. The tube defines a channel extending from the proximal end to an aperture at the distal end. A positioning mechanism is positionable at the distal end of the flexible tube proximate the aperture. The positioning mechanism is configured for movement relative to the distal end of the flexible tube to control a direction at which a treatment instrument extends from the aperture. The positioning mechanism includes an engagement structure configured to maintain a releasable friction fit between a treatment instrument and the positioning mechanism.

In various embodiments, the device may include one or more of the following additional features: wherein the positioning mechanism is configured for lateral deflection relative to the distal end of the flexible tube through rotation about a pin; wherein a pull wire is connected to the positioning mechanism and actuation of the pull wire controls movement of the positioning mechanism; wherein the positioning mechanism comprises an elevator having a ramped surface; wherein the positioning mechanism comprises a block having a lumen therethrough, the lumen housing the engagement structure; wherein the engagement structure comprises one of a grommet, raised protrusions, an o-ring, and an inflatable bladder configured to engage a treatment instrument extending therein to secure the position of a treatment instrument relative to the positioning mechanism; wherein the engagement structure includes a material having a higher coefficient of sliding friction than the flexible tube; wherein the positioning mechanism comprises a clamping mechanism having a first clamping block and a second clamping block movable relative to each other to define a clamping aperture therebetween for receiving a treatment instrument; wherein the engagement structure includes surfaces of the first and second clamping block; wherein a distance between the first and second clamping blocks is adjustable such that an operator can selectively engage and release a treatment instrument during a medical procedure; wherein the clamping mechanism is configured for lateral deflection relative to the distal end of the flexible tube through rotation about a pin; wherein the block is configured for lateral deflection relative to the distal end of the flexible tube through rotation about a pin; wherein the engagement structure is a sleeve; and wherein the position mechanism includes an elevator, and the sleeve at least partially surrounds the elevator.

In another embodiment, a medical device comprises an elongated flexible tube including a distal end and a proximal end. The tube defines a channel extending from the proximal end to an aperture at the distal end. A positioning mechanism is positionable at the distal end of the flexible tube proximate the aperture. The positioning mechanism is configured for lateral deflection relative to the distal end of the flexible tube to control a direction at which a treatment instrument extends from the aperture. A sleeve at least partially surrounds the positioning mechanism and is configured to maintain a releasable friction fit between the sleeve, a treatment instrument extended through the sleeve, and the positioning mechanism.

In various embodiments, the device may include one or more of the following additional features: wherein the positioning mechanism is configured for lateral deflection relative to the distal end of the flexible tube through rotation about a pin; wherein a pull wire is connected to the positioning mechanism and actuation of the pull wire controls lateral deflection of the positioning mechanism; wherein the pull wire extends proximally from the positioning mechanism outside of the sleeve; wherein the pull wire extends proximally from the positioning mechanism inside of the sleeve; and wherein the positioning mechanism comprises an elevator having a ramped surface.

In yet another embodiment, a medical device comprises an elongated flexible tube including a distal end and a proximal end. The tube defines a channel extending from the proximal end to an aperture at the distal end. A positioning mechanism is positionable at the distal end of the flexible tube proximate the aperture. The positioning mechanism is configured for lateral deflection relative to the distal end of the flexible tube to control a direction at which a treatment instrument extends from the aperture. The positioning mechanism includes a lumen extending therethrough configured to receive a treatment instrument therein. The lumen includes an engagement structure configured to maintain a releasable friction fit between a treatment instrument and the positioning mechanism.

In various embodiments, the device may include one or more of the following additional features: wherein the positioning mechanism is configured for lateral deflection relative to the distal end of the flexible tube through rotation about a pin; wherein a pull wire is connected to the positioning mechanism and actuation of the pull wire controls lateral deflection of the positioning mechanism; wherein the engagement structure comprises one of a grommet, raised protrusions, an o-ring, and an inflatable bladder configured to engage a treatment instrument extending therein to secure the position of a treatment instrument relative to the positioning mechanism; wherein the engagement structure includes a material having a higher coefficient of sliding friction than the flexible tube; and wherein the positioning mechanism comprises a clamping mechanism having a first clamping block and a second clamping block movable relative to each other to define a clamping aperture therebetween for receiving a treatment instrument Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Figure 1:
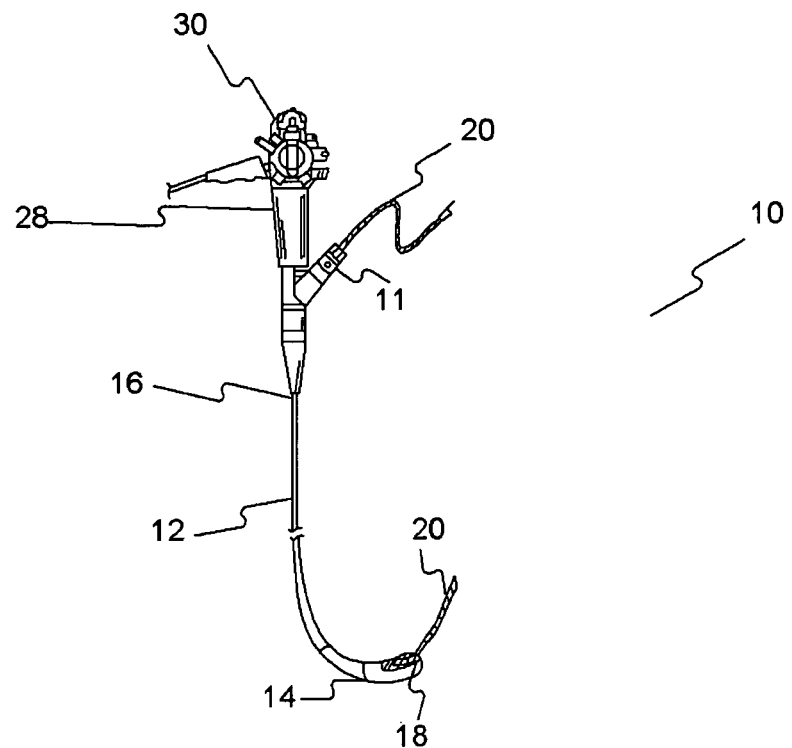
FIG. 1 is a perspective view of a prior art endoscope system.

Reference will now be made in detail to the exemplary embodiments of the invention, examples of which are illustrated in the accompanying drawings. Wherever possible, the same reference numbers will be used throughout the drawings to refer to the same or like parts. The drawing figures of this application are intended to provide a general understanding of the working elements of the underlying system. Accordingly, unless explicitly stated, the figures do not represent a literal depiction of proportional dimensions or the precise locations for the illustrated inter-related components.

According to exemplary embodiments, the invention relates to a medical device for positioning a treatment device and/or viewing a patient's internal body portion. In embodiments that use a treatment device in an endoscopic medical procedure, the treatment device can be advanced through a working channel of an endoscope, including an endoscope specifically designed and/or sized for use with the treatment device, and into a tissue tract. For purposes of this disclosure, "treatment device" or "treatment instrument" includes, for example, any medical device advanced through a working channel of an endoscope and for use during an endoscopic procedure. Exemplary treatment instruments include, but are not limited to, guide wires, cutting or grasping forceps, biopsy devices, snare loops, injection needles, cutting blades, scissors, retractable baskets, retrieval devices, ablation and/or electrophysiology catheters, stent placement devices, surgical stapling devices, and balloon catheters.

FIG. 1 illustrates a known endoscope system. For purposes of this disclosure, "distal" refers to the end further from the device operator during use and "proximal" refers to the end closer to the device operator during use. FIG. 1 depicts an endoscope 10 including a flexible outer tube 12 extending between a distal end 14 and a proximal end 16 of the device. Endoscope 10 includes a treatment device insertion port 11 for receiving a treatment device 20 into a working channel of the endoscope 10. The distal end 14 of the endoscope system 10 includes a side facing operation window 18 that can include visualization and lighting components for viewing during a treatment procedure. In addition, a working channel (not shown) extends within the endoscope 10 and terminates at the operation window 18, thereby allowing the treatment instrument 20 to be extended from the distal end of the endoscope 10. The extension of the treatment instrument 20 at a desired treatment site can be then viewed through the visualization components, which transmit images to the proximal end of the endoscope 10, as known in the art. While FIG. 1 illustrates a side facing operation window 18, both front/forward facing and oblique/intermediate angled windows are known.

Figure 2:
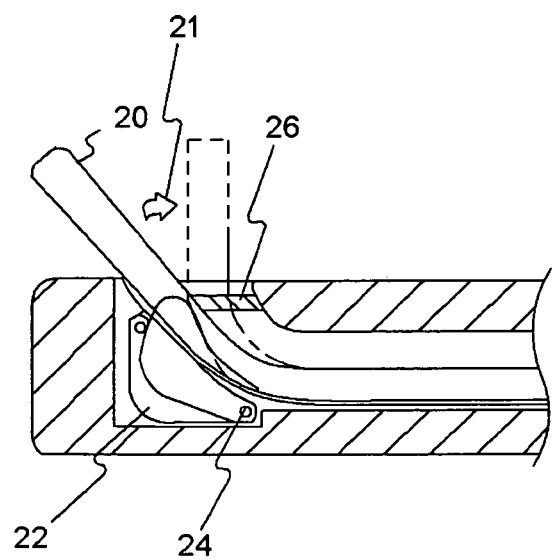
FIG. 2 is a cross-sectional view illustrating the structure of a known elevator device.

FIG. 2 illustrates a cross-sectional view of a distal portion of a known endoscope system including a deflecting lever/elevator device for deflecting a treatment instrument as the instrument is extended beyond a working channel of an endoscope. As seen in FIG. 2, a deflecting lever 22 is rotated clockwise about a pin 24 by means of a pull wire 26 connected to an upper portion of the deflecting lever 22. Upon actuation of the pull wire 26 through proximal movement thereof, the deflecting lever 22 deflects the treatment device 20 in order to alter the angle at which the treatment device 20 exits the endoscope's working channel, resulting in the position of device 20 shown by the dashed lines in FIG. 2. Accordingly, arrow 21 depicts "lateral deflection" of device 20 relative to the underlying endoscope body. By means of pull wire 26, the endoscope operator can control the placement of the treatment instrument 20 as it is positioned during a medical procedure. The operator, however, still needs to manually secure the position of the treatment device 20 relative to the working channel of the endoscope within which it is housed.

As seen in FIG. 1, a handle 28 at the proximal end 16 of the device can include various positioning controls 30 to effectuate bending and rotation of the flexible outer tube 12 for positioning of the device during a medical procedure. In addition, the handle 28 can include a distinct positioning control for actuation of the deflection lever pull wire 26. During a medical procedure such as, for example, an ERCP procedure, the treatment instrument 20 must be precisely inserted into a particular duct in the biliary tree. While the use of a deflection lever 22 is capable of altering the angle at which the treatment device 20 exits the endoscope, precise positioning often requires repeated manipulation of the distal end of the endoscope including the operation window 18 in order to achieve proper placement of the treatment device 20. As noted above, this repeated manipulation of the underlying endoscope 10 and treatment instrument 20 can lead to tissue trauma and unnecessarily prolong the entire medical procedure.

As seen in the embodiment of FIG. 2, the deflection lever 22 is displaceable about a single axis (i.e. the axis coincident with the pin 24). Accordingly, lever 22 is movable to effectuate lateral deflection of the treatment device 20. In some situations, precise manipulation of a treatment device 20 by an elevator lever 22 requires that the position of the treatment device 20 be securely fixed relative to the working channel of the endoscope prior to the actuation of lever 22. For example, where an operator confirms proper placement of a treatment device 20 beyond a treatment window of an endoscope, maintaining the relative position between the treatment device 20 and the endoscope will allow an operator to focus on other positioning tasks. Even where a treatment device 20 is initially in proper position relative to an underlying endoscope, manipulation of positioning mechanisms can improperly transfer force such that a final position of the treatment instrument is undesirably altered.

For example, where the bending stiffness of the treatment device 20 and the desired degree of lever actuation are relatively great, positioning forces applied through a deflection lever 22 can be inaccurately transmitted resulting in proximal displacement of a treatment device 20 within the working channel of the underlying endoscope. Accordingly, in order to prevent such unintended force transfer and displacement of device 20, an operator must manually maintain the relative position of a treatment device 20 and the endoscope while at the same time manipulating the other mechanisms of an endoscope positioning system. Accordingly, there exists a need for a locking or securing mechanism in the medical device arts to selectively secure a position of a treatment instrument relative to a positioning mechanism within an endoscope.

Figure 3A:
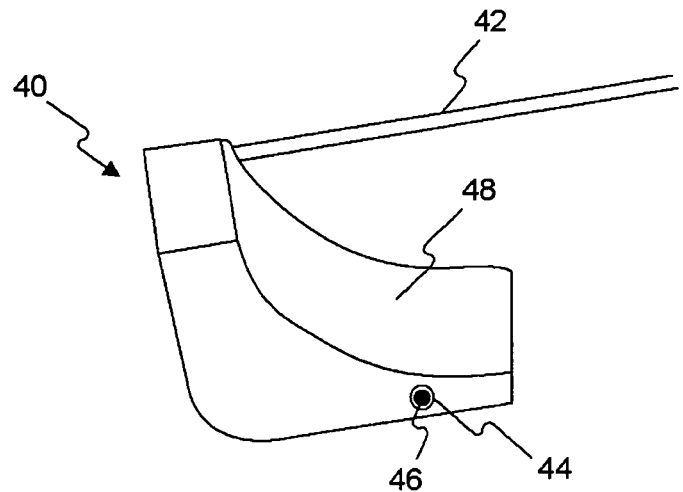
FIG. 3A is a perspective view of an elevator mechanism of an endoscope according to an embodiment of the present invention.

FIG. 3A illustrates an elevator 40 according to an embodiment of the invention. The elevator 40 can be configured for placement within a distal portion of an endoscope in order to effectuate lateral deflection of a treatment instrument during a medical procedure. For example, elevator 40 may include a pull wire 42 connected to an upper side portion thereof and a recess 44 that receives a pin 46 about which the elevator 40 can rotate upon proximal actuation of pull wire 42. In embodiments utilizing side facing endoscope window portions, the elevator 40 can include a ramped surface 48 for directing the path of a treatment instrument at the distal end of an endoscope towards the window portion. Ramped surface 48 may further include a curved concave shape configured to maintain contact with a treatment instrument 20 extended therein during a medical procedure. The curved surface 48 of the elevator 40 acts as the surface for transferring a deflection force against a treatment instrument 20, for example, during extension of the treatment instrument 20.

Figure 3B:
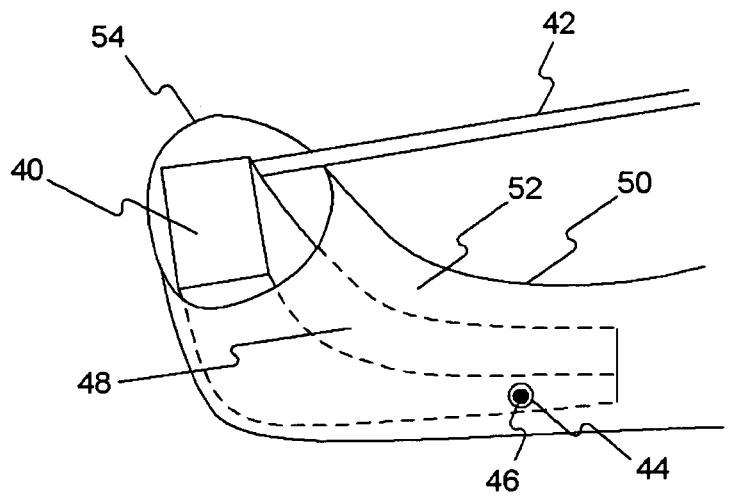
FIG. 3B is a perspective view of an elevator and sleeve arrangement of an endoscope according to an embodiment of the present invention.

FIG. 3B illustrates elevator 40 of FIG. 3A with a mechanism for securing a position of a treatment instrument within an endoscope and relative to elevator 40. In particular, elevator 40 is surrounded by a sleeve element 50. Sleeve 50 includes an inner lumen 52 housing the elevator 40, a distal opening 54, and a proximal opening (not shown). As seen in FIG. 3B, distal opening 54 exposes a portion of elevator 40, while surrounding a remaining portion of the elevator represented by dashed lines. The sleeve 50 can be sized to releasably slip over the elevator 40 in order to present a friction fit arrangement between the elevator 40 and a treatment device inserted within the sleeve 40. Furthermore, the lumen 52 and opening 54 of sleeve 50 can be sized to provide a predetermined clearance area through which a treatment device extends during an endoscopic treatment procedure.

The sleeve 50 can be formed of a material providing a high coefficient of sliding friction against a treatment device such that the sleeve 50 maintains the relative position between the treatment device and elevator without requiring active fixation by an operator at a proximal end of an endoscope. Both the size of sleeve 50 and the materials forming the sleeve 50 can be selected to maintain a releasable friction fit arrangement, whereby a treatment instrument extended therethrough remains securely fixed relative to the underlying elevator 40 unless a sufficient force is a directed to the treatment device to overcome the friction force holding the treatment instrument in place. Sleeve 50 may be formed, for example, from any known materials commonly used in medical device components suitable for providing a relatively high coefficient of sliding friction relative to a treatment device. Exemplary materials include, but are not limited to, polymeric materials such as, polytetrafluoroethylene (PTFE), Nylon, synthetic rubbers, silicone, and TPE (thermo plastic elastomers). For example, suitable TPEs include those manufactured and sold by Kraton Polymers U.S. LLC of Houston, Tex. In addition, the desirable effects of sleeve 50 may be enhanced by machining, molding, or otherwise manipulating the interior surface such that it exhibits a more roughened texture. For example, the selected material for sleeve 50 can have its frictional properties enhanced by adding a component providing a specific textural feature to the sleeve composition.

In addition, the material and size of sleeve 50 could be selected to exhibit a predetermined amount of flexibility to allow bending and internal movement of parts, such as, for example, movement of pull wire 42 therein. Pull wire 42, depicted as connected to an upper side portion of the elevator 40, can extend outside of sleeve 50 such that controlled proximal actuation of pull wire 42 does not contact or interfere with the surface of sleeve 50. Alternatively, sleeve 50 can be sized to accommodate the pull wire 42 as it extends proximally from the elevator within lumen 52 of sleeve 50. In either embodiment, proximal actuation of pull wire 42 effectuates rotation of both elevator 40 and the surrounding sleeve 50.

Figure 3C:
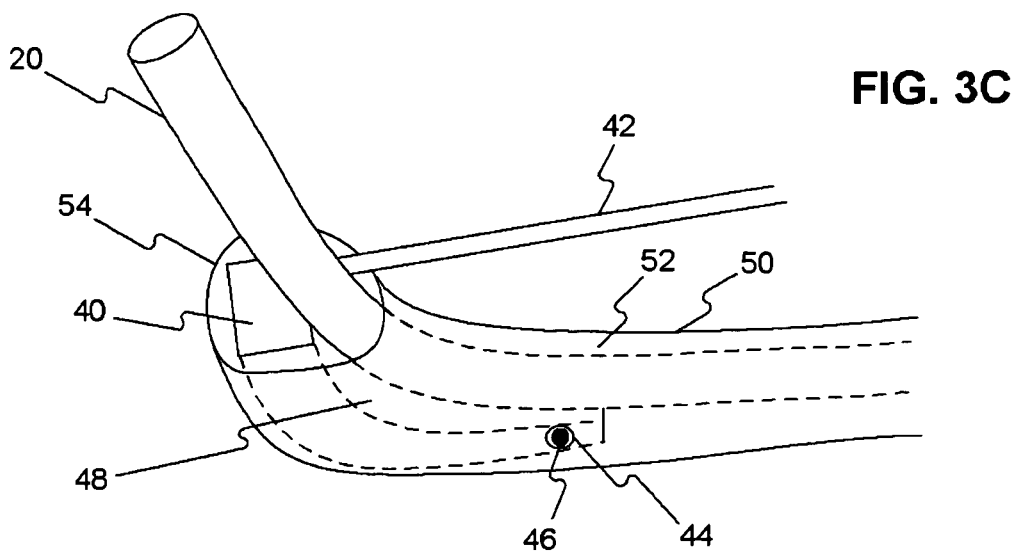
FIG. 3C is a perspective view of an elevator, sleeve, and treatment instrument arrangement of an endoscope according to an embodiment of the present invention.

FIG. 3C illustrates elevator 40 surrounded by sleeve element 50, through which a treatment instrument 20 is extended. As noted above, the size and material for sleeve 50 are selected to maintain a releasable friction fit arrangement whereby, a treatment instrument, such as for example, device 20, extended therethrough remains securely fixed relative to the underlying elevator 40. The position of treatment instrument 20 relative to elevator 40 is maintained unless a sufficient force is directed to the treatment instrument 20 to overcome the friction force holding the treatment instrument 20 in place. For example, during a medical procedure, an operator can maintain a desired position of treatment instrument 20 relative to elevator 40 (and therefore the entire underlying endoscope) without being required to manually secure the position of the treatment instrument 20 relative to the underlying endoscope. For example, the operator may not have to manually hold the proximal end of the instrument 20 relative to the endoscope during manipulation of elevator 40. Accordingly, through the use of sleeve 50, an operator can utilize a hand for manipulation purposes or other purpose, rather than securing the position of a treatment instrument 20 relative to an endoscope.

As noted above, sleeve 50 is releasably slipped over the elevator 40 prior to use in an endoscopic procedure. In addition, sleeve 50 can be particularly sized to provide a friction fit arrangement with a particular treatment device 20. Therefore, sleeve 50 may be a disposable auxiliary element for use in an endoscope system configured to facilitate more precise positioning of a particular treatment device 20. Sleeve 50 may be a disposable (i.e. single use) element in a reusable underlying endoscope. For example, a particularly sized sleeve 50 could be purchased along with a correspondingly sized treatment device 20. The sleeve 50 could be universally sized for surrounding a range of known elevator devices, while being particularly sized to correspond to the accompanying treatment device 20. Alternatively, sleeve 50 could be especially sized to correspond to a particular size endoscope channel or elevator, and treatment device 20. In addition, as a further alternative, the sleeve 50 could be reusable with the elevator device it surrounds and the sleeve 50 could be sized to accommodate and provide a friction fit for a range of known treatment devices 20.

Figure 4:
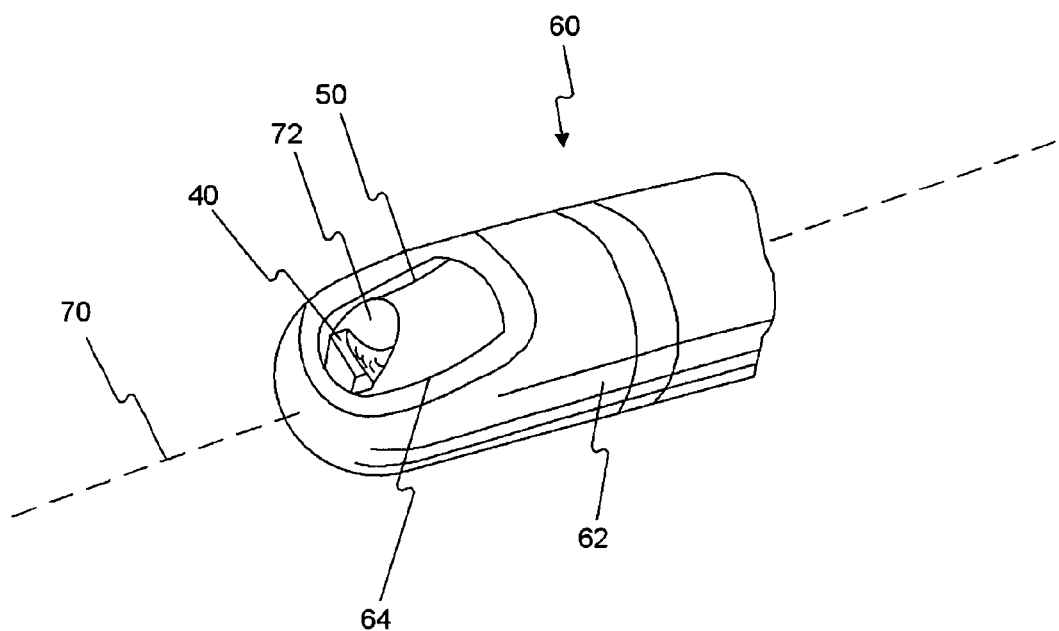
FIG. 4 is a perspective view of a distal part of an endoscope including an elevator and sleeve arrangement according to an embodiment of the present invention.

FIG. 4 illustrates a perspective view of a distal part of an endoscope 60 including an arrangement of an elevator 40 and sleeve 50 according to an embodiment of the present invention. The distal portion of endoscope 60 includes an exterior flexible outer tube 62, a side facing operation window aperture 64, and a working channel forming a lumen within the endoscope 60 and extending from the proximal end of the endoscope 60 and terminating at the operation window aperture 64. The flexible outer tube 62 extends along a longitudinal axis 70. The working channel extends proximally through the endoscope 60 to a proximal working channel access port (not shown) through which a treatment instrument can be tracked. As seen in FIG. 4, sleeve 50 can be releasably slipped over the elevator 40 and sized to provide a predetermined clearance area 72 through which a treatment device extends during an endoscopic treatment procedure. As noted above, this predetermined clearance area 72 and the particular material of formation for sleeve 50 provide the benefits of a friction fit arrangement for more precisely maintaining the position of a treatment device relative to the underlying endoscope 60.

Figure 5:
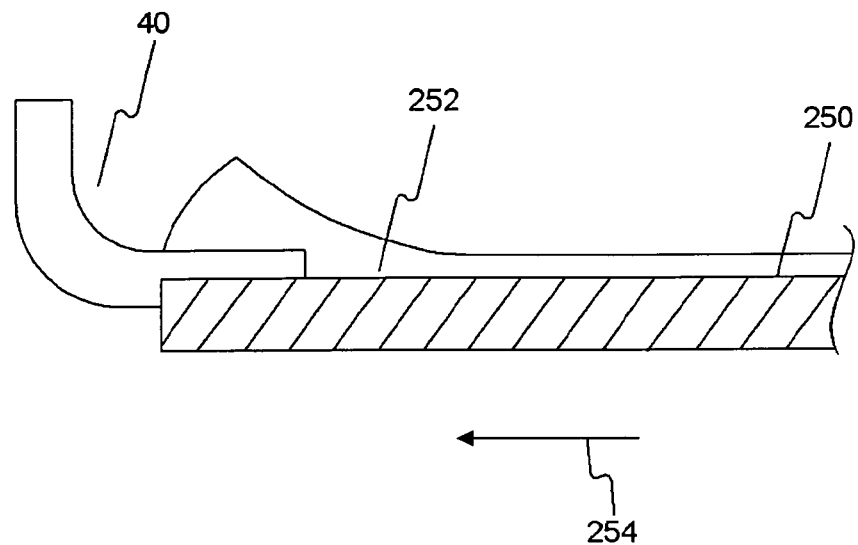
FIG. 5 illustrates one embodiment of a sleeve design that facilitates the enclosure of an elevator.

FIG. 5 illustrates one embodiment for a sleeve designed for interaction with an elevator 40 to enhance the stability and positioning of an underlying treatment instrument. FIG. 5 illustrates a sleeve 250 configured for enclosing an elevator component such that upon final assembly the elevator 40 and sleeve 250 achieve an arrangement similar to that of FIG. 4. Sleeve 250 includes a split tube portion 252 that provides an enlarged opening at one end of the sleeve 250. During initial assembly of the sleeve 250 and elevator 40, the sleeve 250 engages and surrounds the elevator 250 initially about the enlarged opening in the direction of arrow 254. The enlarged opening guides the elevator within the non-slit portion of the sleeve 254. After complete enclosure of the elevator, the excess, slit portion of sleeve 254 can be excised and discarded.

Figure 6:
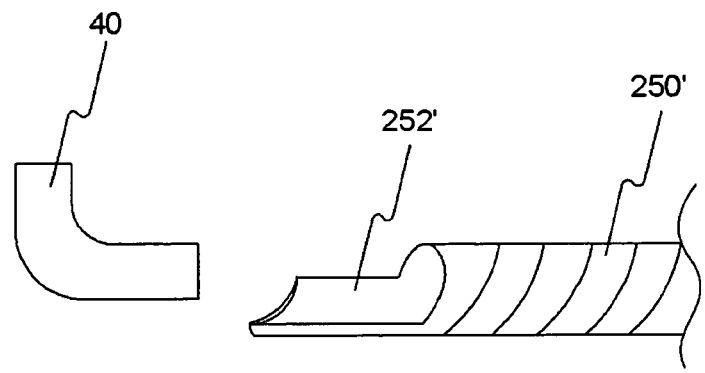
FIG. 6 illustrates another embodiment of a sleeve design that facilitates the enclosure of an elevator.

FIG. 6 illustrates another embodiment that facilitates and guides the interaction and engagement between a sleeve and an elevator component. FIG. 6 depicts an elevator 40 and a sleeve 250' that includes a cutout portion 252'. By virtue of cutout portion 252', an enlarged opening is exposed leading to the interior of sleeve 250'. As such, elevator 40 is more easily engaged with sleeve 250' during initial assembly. Just as in the embodiment of FIG. 5, after complete enclosure of the elevator, the excess portion of sleeve 250' can be excised and discarded.

Figure 7:
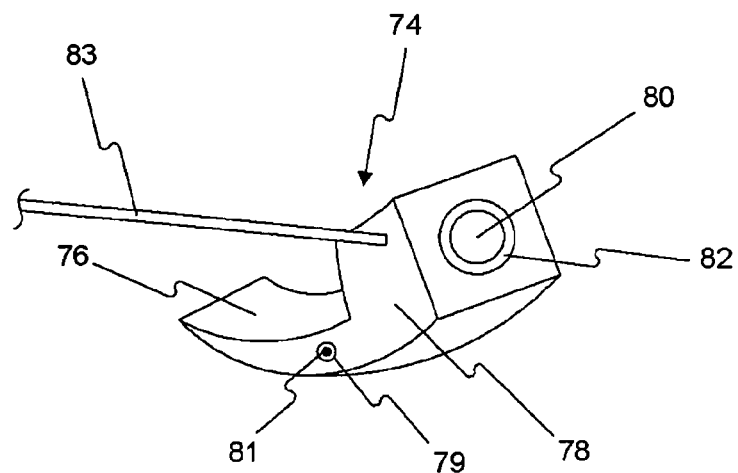
FIG. 7 illustrates a perspective view of a treatment instrument positioning mechanism according to another embodiment of the present invention.

FIG. 7 illustrates a perspective view of a treatment instrument positioning mechanism according to another embodiment of the present invention. FIG. 7 illustrates a working channel insert, or elevator, 74 configured for placement within and at the distal end of a working channel of an endoscope. In one exemplary embodiment, elevator 74 may include a proximal ramped segment 76 leading to a distal positioning block 78. When installed within an endoscope, segment 76 is configured to guide a treatment instrument towards block 78 and into a hollow lumen 80 extending through block 78. Segment 76 may include a ramped surface, which may be grooved, to receive and guide a treatment instrument. The ramped surface of segment 76 leads to lumen 80 extending through positioning block 78.

In the illustrated example, lumen 80 through positioning block 78 includes an engagement structure configured for securing a treatment instrument positioned therein relative to the positioning block 78. In one illustrated embodiment, the engagement structure includes an eyelet, or grommet 82, of relatively firm material to strengthen the lumen 80 and configured to engage a treatment instrument passed therethrough. Grommet 82 can be formed of a material providing a high coefficient of sliding friction against a treatment device such that the grommet maintains the relative position between the treatment device and positioning block 78 without requiring fixation by an operator at a proximal end of an endoscope. Both the size of grommet 82 and the materials forming the grommet 82 are selected to maintain a releasable friction fit arrangement, whereby a treatment instrument extended through the lumen 80 of positioning block 78 remains securely fixed relative to the positioning block 78 unless a sufficient force is a directed to the treatment device to overcome the friction force holding the treatment instrument in place.

In use, insert 74 with positioning block 78 is configured to act as an elevator positioning mechanism, for example, such that the insert 74 can be rotated to exhibit lateral deflection in order to position a treatment instrument beyond a treatment window of an endoscope. For example, the insert 74 can be formed to include a recess 79 for receiving a pin 81 therein about which the insert 74 can be rotated. Just as in the previously described arrangement, rotation of insert 74 can result in controlled lateral deflection of a treatment instrument extending within the lumen 80 of positioning block 78. An exemplary mechanism for rotating the insert 74 relative to the pin 81 comprises a pull wire 83 connected to the positioning block 78 and extending proximally within an endoscope. Proximal actuation of the pull wire 83 thereby controls a deflection angle of a treatment instrument.

In addition to the above described embodiment, the rotation and angular orientation of insert 74 with positioning block 78 relative to a window of an underlying endoscope device, for example, can be manipulated through various positioning mechanisms. For example, the orientation at which grommet 82 leads a treatment instrument therethrough can be altered through actuation of an inflatable cuff element positioned below the positioning block 78. Alternative mechanisms for manipulating the orientation of insert 74 include, but are not limited to, the use of pull wire arrangements, a wedge (e.g., an included plane) movable beneath the insert to engage and displace the insert, and a movable cam device beneath the elevator to engage and displace the insert.

In another embodiment, an elongated channel, groove, or flexible tube may be formed integrally with the insert 74. The channel, for example, may extend proximally from the insert and towards the proximal end of an endoscope and within a working channel of an endoscope. Upon placement of the channel and insert within an endoscope, a treatment instrument can be inserted and guided within the elongated channel towards and into lumen 80. Accordingly, in such an arrangement, a treatment instrument is carefully directed at a proximal end of an endoscope to extend through insert 74 and its elongated channel for precise placement at a treatment site. Additional configurations may include an arrangement where the extended insert is displaceable within an internal lumen of the underlying endoscope.

The insert 74 may be configured as a disposable manipulation tool for use with a particular size treatment instrument. Such a single use mechanism is advantageous in that is provides the benefits of a positioning mechanism particularly configured for positioning and placement of a corresponding treatment instrument. In addition, the disposable quality of the insert 74 can provide the added benefits of maintaining a sterile device with less parts being reused in an endoscope and therefore less chance of patient cross-contamination.

The arrangement for the engagement structure should not, however, be limited to the above described grommet structure. For example, the engagement structure in the lumen of a positioning block may include a pattern of raised bumps, ribs, or other protrusions, sized and spaced to engage a particular treatment instrument through a friction providing surface. In addition, the engagement structure could comprise an O-ring of a particular size and material configured to engage and secure a treatment instrument therein. The engagement structure also could comprise a friction enhancing material or coating applied to the surface defining the lumen of the positioning block.

Figure 8:
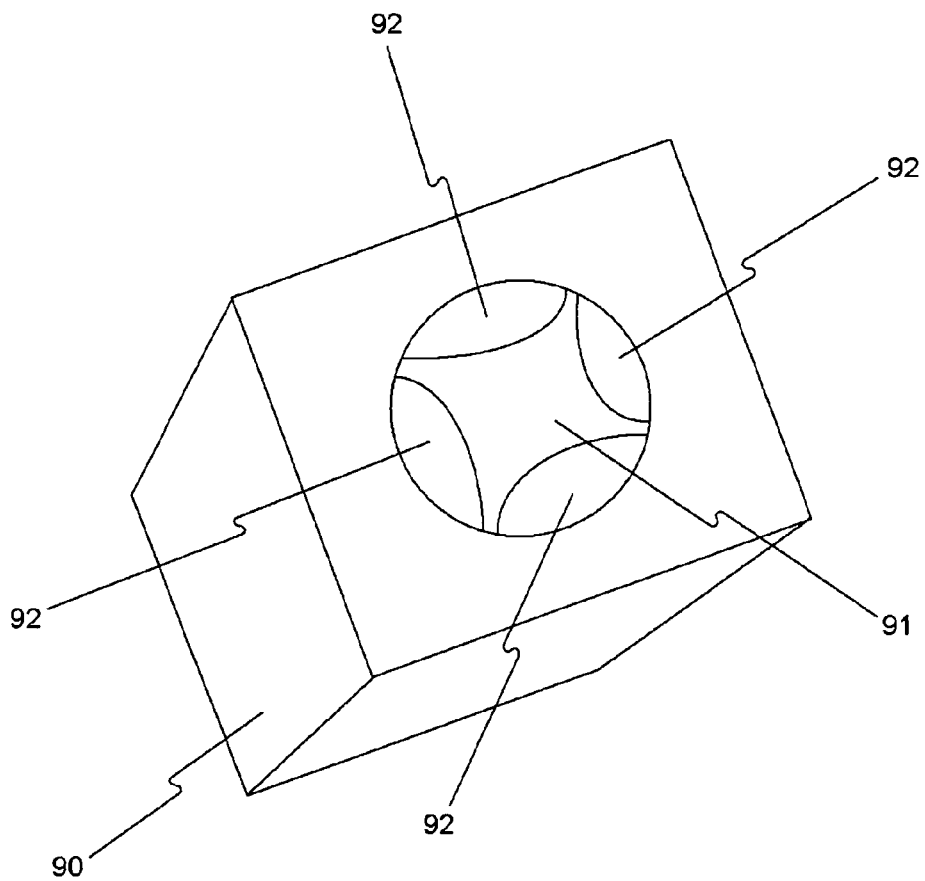
FIG. 8 illustrates a perspective view of a distal portion of a treatment instrument positioning mechanism according to another embodiment of the present invention.

As seen in FIG. 8, another example of an engagement structure is illustrated. FIG. 8 illustrates a positioning block 90 including an internal lumen 91 for receiving a treatment instrument therein. The internal lumen can include a pattern of inflatable bladders 92 arranged therein. Bladders 92 can be configured for controlled inflation by introducing fluid or gas into the bladders through a system of ports as would be apparent to one of ordinary skill in the art. Bladders 92 can be formed of a material exhibiting a high coefficient of sliding friction relative to a particular treatment instrument 20. Accordingly, controlled inflation of the bladders 92 can result in securing a treatment instrument 20 relative to the positioning block. When further displacement and positioning of the treatment instrument 20 is required, the engaging bladders 92 can be adjustably deflated in order to provide clearance within the lumen 91. Accordingly, the bladders 92 provide an adjustable securing mechanism for precisely positioning a treatment instrument 20 relative to a positioning block and an underlying endoscope. In an alternative arrangement, the bladders 92 need not be inflatable. Instead, they may be merely comprised of a resilient material such that they can grab and engage a particular treatment instrument, yet still allow tool advancement when desired. In yet another alternative arrangement, the individual bladders 92 can be replaced with a single ring-shaped annular inflatable bladder having a central opening that receives a treatment instrument 20.

Figure 9:
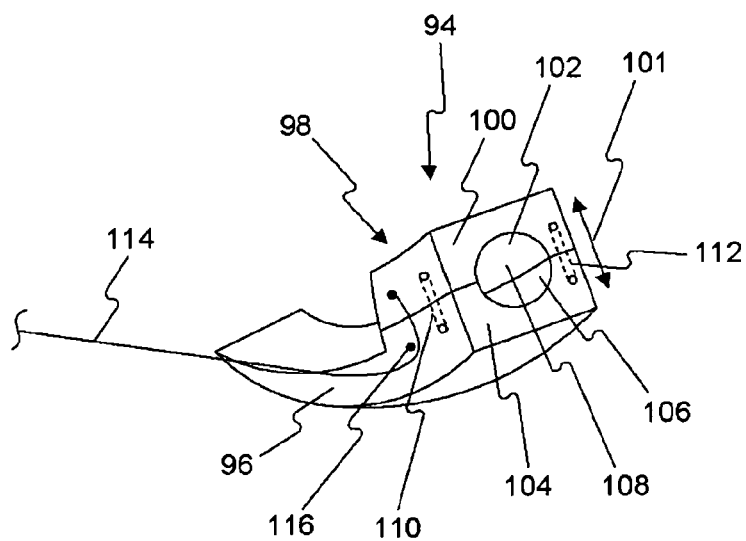
FIG. 9 illustrates a perspective view of a treatment instrument positioning mechanism according to another embodiment of the present invention.

FIG. 9 illustrates an additional working channel insert 94 including a proximal segment 96 leading to a distal clamping mechanism 98. In one exemplary embodiment, insert 94 may include a proximal ramped segment 96 leading to a distal aperture 108. When installed within an endoscope, ramped segment 96 is configured to guide a treatment instrument towards clamping mechanism 98 and into and through aperture 108. The ramped surface of segment 98 may be grooved to receive and guide a treatment instrument. The ramped surface of segment 96 leads to aperture 108 extending through clamping mechanism 98.

As seen in FIG. 9, clamping mechanism 98 may include an upper clamping block 100 having an upper recess portion 102 and a lower clamping block 104 having a lower recess portion 106, arranged to provide an internal aperture 108 between the upper and lower clamping blocks 100 and 104. Upper and lower clamping blocks 100 and 104 are configured for adjustable movement relative to each other (in the directions of arrows 101). Since the distance between upper and lower clamping blocks 100 and 104 is adjustable, different sizes of treatment instruments can be accommodated therein. In addition, the upper and lower clamping blocks 100 and 104 can be adjusted to provide a varying clamping force to a treatment instrument extended through aperture 108. The movement is along, for example, a left guide post 110 and a right guide post 112 extending through side portions of the upper and lower clamping blocks 100 and 104.

As one example, upper and lower clamping blocks 100 and 104 are configured for adjustable movement relative to each other along left and right guide posts 110 and 112 through a pull wire 114. A compression spring (not shown) can be provided to maintain the upper and lower clamping blocks 100 and 102 at a specific distance away from each other, such that a clamping force must overcome the resistance provided by the compression spring. While a pull wire 114 may be provided on each side of a clamping mechanism 98, only one wire 114 is illustrated for purposes of simplicity. Pull wire 114 may be fixed to upper clamping block 100 and extend to lower clamping block 104 where it curves proximally about pull wire post 116, such that proximal actuation of pull wire 114 is transmitted into a force which pulls (against the force of a compression spring, for example, provided therebetween) upper and lower clamping blocks 100 and 104 together.

Accordingly, the size of internal aperture 108 between the upper and lower clamping blocks 100 and 104 can be adjusted to receive treatment instruments of varying sizes. In addition, the adjustment of clamping blocks 100 and 104 allows for the position of a treatment instrument to be maintained relative to the remainder of an underlying endoscope during a positioning procedure. Accordingly, as noted above with regard to the previously explained embodiments, adjustably securing a treatment instrument relative to an underlying endoscope potentially frees an operator's hand for controlled manipulation of alternate elements.

The surface materials forming the recess portions 102 and 106 can be selected to provide a relatively high coefficient of sliding friction such that a treatment instrument extended through the aperture 108 remains securely fixed relative to the clamping mechanism 98 unless a sufficient force is a directed to the treatment device to overcome both the friction force of the surface materials and the clamping force holding the treatment instrument in place. For example, the surfaces of recess portions 102 and 106 may include a friction enhancing coating.

Just as described in the previous arrangements, the rotation and angular orientation of insert 94 relative to an treatment window of an underlying endoscope device, for example, can be manipulated through various positioning mechanisms. For example, the orientation at which insert 94 leads a treatment instrument through aperture 108 can be manipulated through a manipulation of a pull wire mechanism or an inflatable cuff element positioned below the clamping mechanism. In addition, the insert 94, including the segment 96 and clamping mechanism 98, may be configured as a disposable manipulation tool for use with a particular size treatment instrument. Such a single use mechanism is advantageous in that is provides the benefits of a positioning mechanism particularly configured for positioning and placement of a corresponding treatment instrument.

Figure 10:
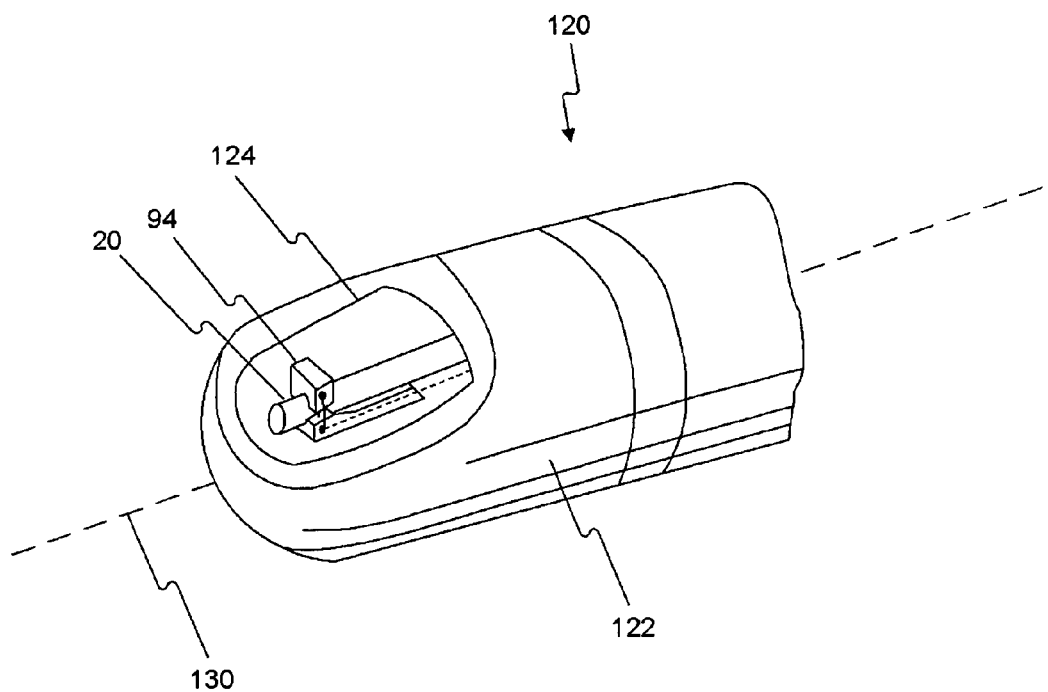
FIG. 10 is a perspective view of a distal part of an endoscope including the positioning mechanism of FIG. 9 according to an embodiment of the present invention.

FIG. 10 illustrates a perspective view of a distal part of an endoscope 120 including an arrangement of an insert 94 according to an embodiment of the present invention. The distal portion of endoscope 120 includes an exterior flexible outer tube 122, a side facing operation window aperture 124, and a working channel forming a lumen within the endoscope 120 and extending from the proximal end of the endoscope 120 and terminating at the operation window aperture 124. The flexible outer tube 122 extends along a longitudinal axis 130. The working channel extends proximally through the endoscope 120 to a proximal working channel access port (not shown) through which a treatment instrument can be tracked. As seen in FIG. 10, clamping mechanism 98 is adjusted to receive a treatment instrument 20 therein. As an additional positioning feature, the insert 94 (or any of the previously explained embodiments) can itself by configured for movement through more than one degree of freedom, such as, for example, through a system as described in co-pending U.S. application Ser. No. 11/779,532, filed Jul. 18, 2007, the complete disclosure of which is hereby incorporated by reference.

Figure 11:
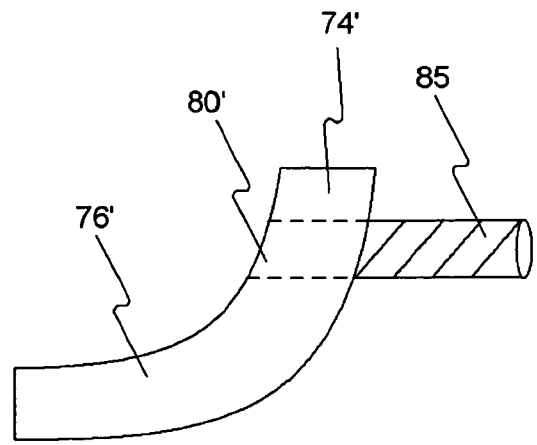
FIG. 11 illustrates a distal portion of a treatment instrument positioning mechanism according to another embodiment of the present invention.

FIG. 11 illustrates a working channel insert, or elevator, 74' configured for placement within and at the distal end of a working channel of an endoscope. As illustrated, elevator 74' may include a proximal ramped segment 76'. When installed within an endoscope, insert 74' serves to receive a treatment instrument within a hollow lumen 80' (illustrated in dashed lines) extending therethrough. On the convex side of the elevator insert 74', the lumen 80' leads to an extension tube 85. The extension tube 85 can be comprised of the same material as that used for sleeve 50 described above. As a result, the tube 85 serves to engage, hold, and maintain a treatment instrument's relative location during positioning. Upon actuation of the insert 74', which causes deflection of the insert 74', an operator can carefully control the angular orientation of a treatment instrument positioned within lumen 80' and sleeve 85.

Figure 12:
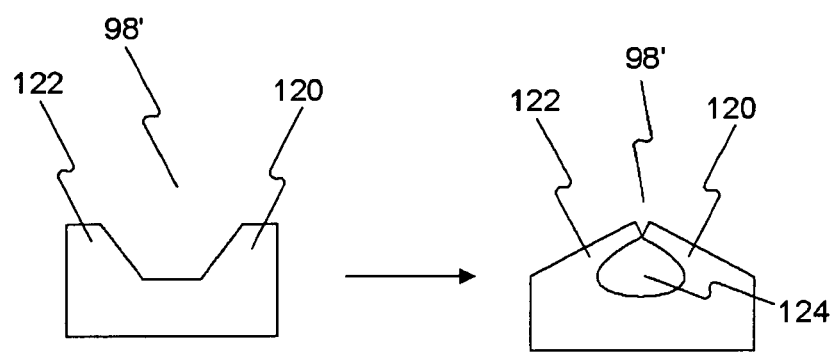
FIG. 12 illustrates one component for use in positioning a treatment instrument according to another embodiment of the present invention.

FIG. 12 illustrates one alternative clamping component arrangement for use in a clamping system similar to that described earlier in FIG. 9. FIG. 12 illustrates one component of an alternative clamping mechanism 98'. The illustrated component includes two clamping arms 120 and 122, respectively. The two arms 120, 122 are arranged such that they exhibit an open configuration during rest (i.e., without any external force acting on the clamping mechanism 98'). For example, the left side of FIG. 12 illustrates mechanism 98' in a resting condition. The right side of FIG. 12 illustrates the clamping arms 120 and 122 moved together in a closed, or clamped, configuration. In the closed configuration, a treatment instrument can be inserted through, positioned, and maintained in the enclosure 124 formed by virtue of the closed clamping arms 120 and 122. The treatment instrument can be inserted prior to or after closure of clamping arms 120, 122.

The mechanism 98' can transition from the open to the closed configuration in any manner know to one having ordinary skill in the art. For example, a number of gear arrangements can be provided in order to convert axial displacement of pull wires into the rotational displacement necessary to move the arms 120 and 122 to the configuration on the right side of FIG. 12. In addition, the movement of arms 120, 122 can be effectuated by implementing an electronic transducer, such as, for example, a piezoelectric transducer that results in the closed configuration of FIG. 12 by providing a predetermined voltage and current to the piezoelectric elements provided in arms 120, 122. In addition, any number of spring arrangements may be provided, such as, for example, a spring arrangement similar to that of a movable clothes-pin jaw arrangement.

Figure 13:
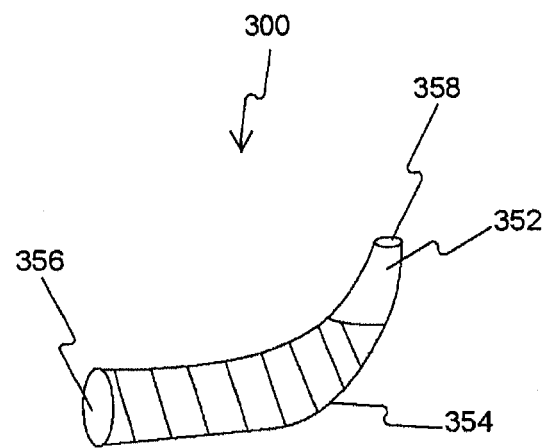
FIG. 13 illustrates a distal portion of a treatment instrument positioning mechanism according to another embodiment of the present invention.

FIG. 13 illustrates an alternative working channel insert, or elevator, 300 configured for placement within and at the distal end of a working channel of an endoscope. As illustrated, elevator 300 may comprise a two-part curved tube configuration. A first, proximal tube segment 354, is comprised of a relatively rigid material formed in a ramped, or curved internal configuration. For example, as seen in FIG. 13, the proximal tube segment 354 may be curved to provide a proximal ramped segment. When installed within an endoscope, elevator 300 serves to receive a treatment instrument proximally within the proximal tube opening 356.

The elevator 300 can be manipulated and rotated in the same manner as described above (or below) in any of the other elevator arrangements. The elevator 300 includes a second, distal portion 352 comprised of relatively flexible, yet resilient material. For example, portion 352 may be comprised of a resilient elastic material that expands to releasably enclose a treatment instrument when it is extended beyond the proximal, relatively rigid portion 354. During a procedure, treatment instrument 20 is positioned beyond distal opening 358 such that the resilient material of portion 352 engages and holds a treatment instrument relative to the elevator 300 and the rest of the underlying endoscope. Accordingly, the second portion 352 may be sized such that the desired treatment instrument fits through the proximal portion, yet is still releasably engaged by the distal portion 352.

Figure 14A:
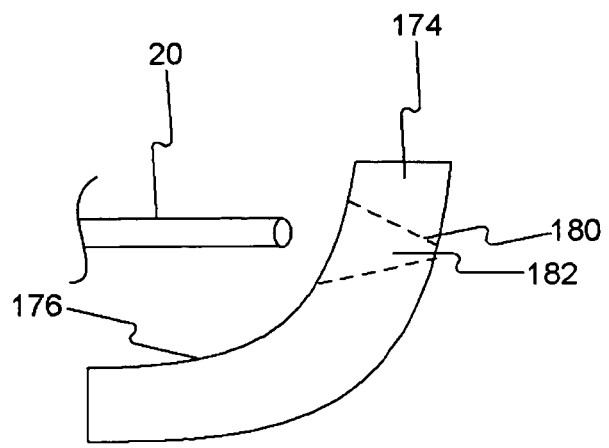
FIG. 14A illustrates a distal portion of a treatment instrument positioning mechanism prior to insertion of a treatment instrument.
Figure 14B:
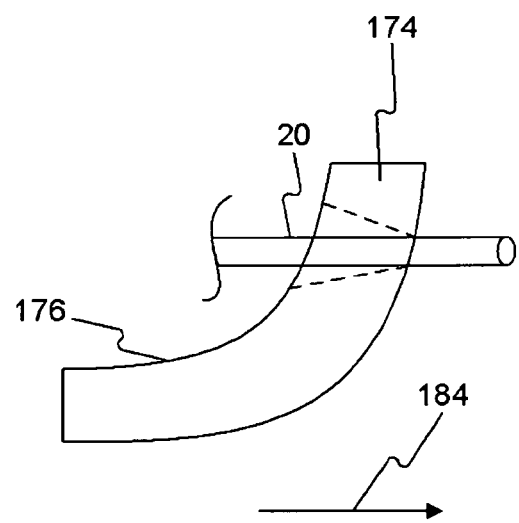
FIG. 14B illustrates a distal portion of a treatment instrument positioning mechanism after insertion of a treatment instrument.

FIGS. 14A and 14B illustrate a working channel insert, or elevator, 174 configured for placement within and at the distal end of a working channel of an endoscope. As illustrated, elevator 174 may include a proximal ramped segment 176. When installed within an endoscope, insert 174 serves to receive a treatment instrument within a hollow lumen 180 (illustrated in dashed lines) extending therethrough. The lumen 180 includes a taper 182. The taper 182 transitions from an enlarged opening on the concave side of the elevator insert 174, leading to a smaller exit opening on the convex side of the elevator insert 174. As seen in FIG. 14B, the lumen 180 is configured to receive a treatment instrument 20. The relative location of the ramp 176 and the lumen 180 facilitate the precise guiding and positioning of a treatment instrument therein. As seen in FIG. 14B, the treatment instrument 20 is guided up ramped surface 176 and into lumen 180 in the direction of arrow 184.

Figure 15A:
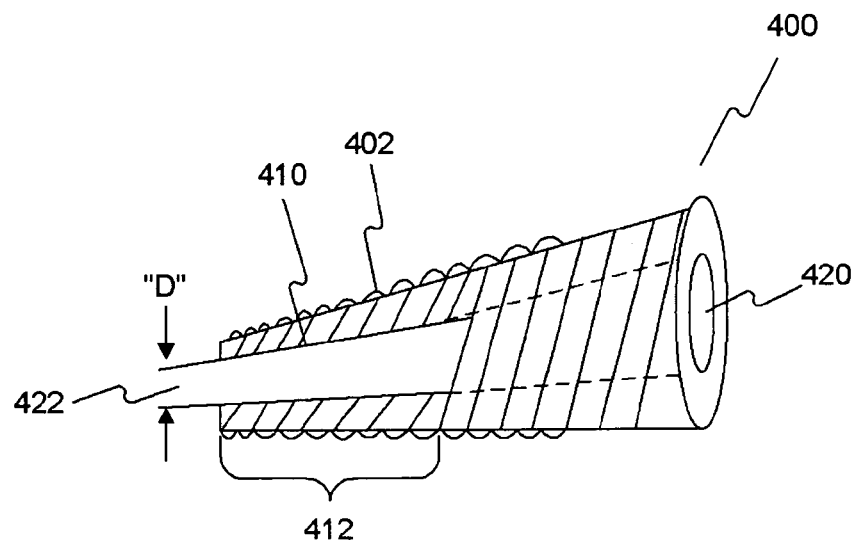
FIG. 15A illustrates one component for use in positioning a treatment instrument according to another embodiment of the present invention.
Figure 15B:
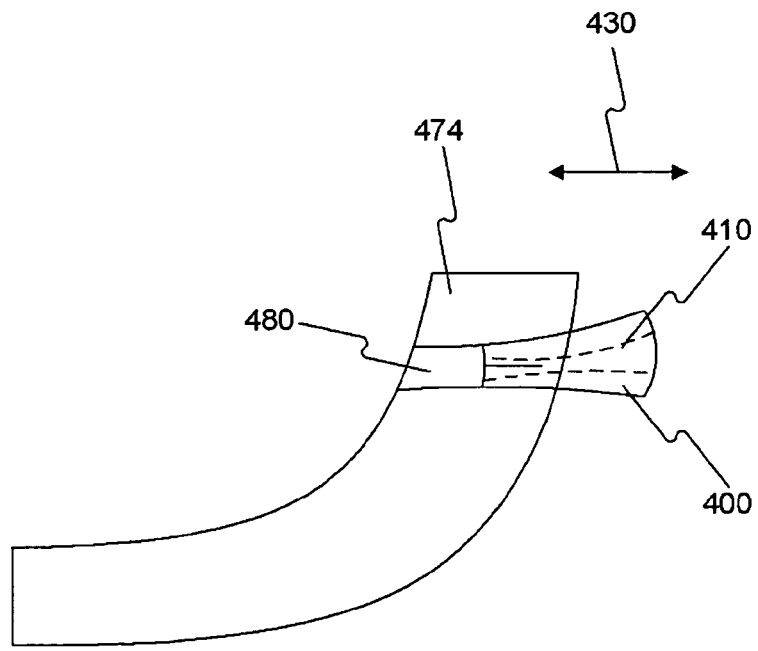
FIG. 15B illustrates a distal portion of a treatment instrument positioning mechanism incorporating the component of FIG. 15A.

FIGS. 15A and 15B illustrate an alternative working channel insert, or elevator device configured for placement within and at the distal end of a working channel of an endoscope. More particularly, the embodiment of FIGS. 15A and 15B provides an insert similar to that described above in FIG. 7, yet including an alternative arrangement configured to provide a mechanism for adjustably clamping a treatment instrument 20.

As seen in FIG. 15B, elevator 474 includes a lumen 480 for receiving a treatment instrument therein. Lumen 480 houses an insert 400 that includes an internal lumen 410 (depicted in dashed lines) that is adjustable to receive and releasably clamp treatment instruments of differing sizes and profiles. With reference to FIG. 15A, the insert 400 may include a proximal portion 412 defining a slit formed therein such that the internal lumen 410 is exposed on at least two sides. The exterior surface of portion 412 along insert 400 can include external threads 402 configured for corresponding engagement with internal threads within lumen 480.

Lumen 410 includes a proximal opening 422 and a distal opening 420 for allowing passage of a treatment instrument therethrough. In addition, lumen 410 is shaped such that it exhibits a diameter "D" at its proximal end. As seen in FIG. 15B, when insert 400 is threadably received within lumen 480, the size of the lumen 410 can be adjusted depending on the extent of insertion of insert 400 within lumen 480. In other words, due to the tapered profile of the insert 400 (tapering in from the distal end to the proximal end), continued rotation of the insert 400 within the lumen 480 causes a reduction of the diameter "D" distance. Thus, depending on the extent of rotation of insert 400 within lumen 480, the diameter distance "D" can be regulated to specifically correspond to the profile of a specific treatment instrument. Therefore, the insert 400 provides a device for securing different sized treatment instruments during insertion. As noted above with regard to the previously explained embodiments, adjustably securing a treatment instrument relative to an underlying endoscope potentially frees an operator's hand for controlled manipulation of alternate elements.

The materials forming the internal surface of lumen 410 can be selected to provide a relatively high coefficient of sliding friction such that a treatment instrument extended through the apertures 422 and 420 remains securely fixed unless a sufficient force is a directed to the treatment device to overcome both the friction force of the surface materials and the clamping force holding the treatment instrument in place. For example, the surfaces of lumen 410 may include a friction enhancing coating.

Figure 16:
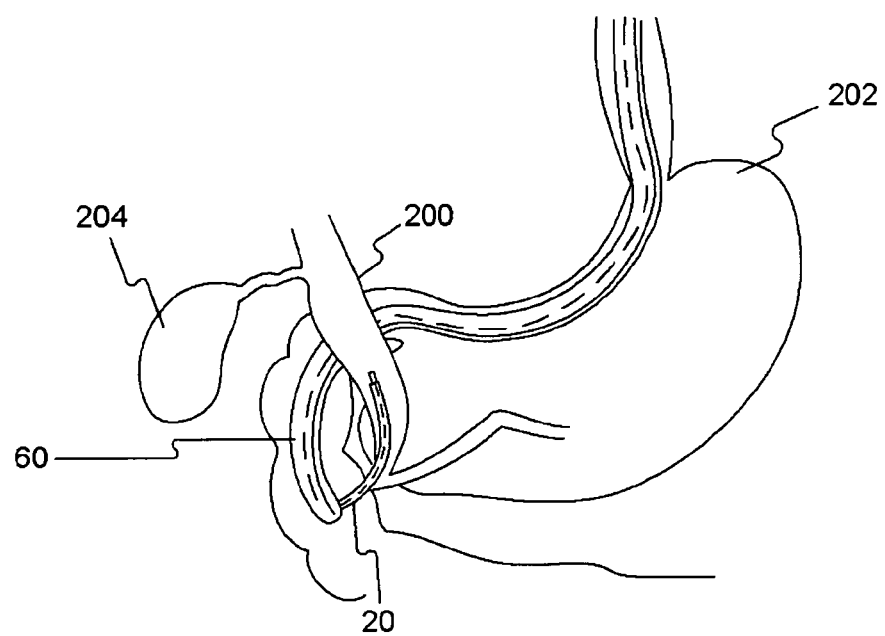
FIG. 16 illustrates the positioning of an endoscope and treatment device within a patient's body portion.

FIG. 16 illustrates the positioning of an endoscope 60 or 120 and a treatment device 20 within a patient's body portion. In particular, FIG. 16 depicts the extension of a treatment instrument 20 within a particular bile duct 200 during an ERCP procedure. As seen in FIG. 16, the endoscope 60, for example, is inserted and extended through a patient's stomach 202 such that the distal end and aperture 64 (not shown) of endoscope 60 are positioned in close relation to a particular bile duct 200 leading to, for example, gall bladder 204. As seen in FIG. 16, treatment instrument 20 is extended beyond the internal working channel of endoscope 60. The treatment instrument 20 can then be precisely manipulated as described above with regard to FIGS. 3A-8.

Precise manipulation of treatment instrument 20 allows for more precise positioning and location of instrument 20 such as, for example, during placement of instrument 20 within a particular bile duct 200 of interest. More precise manipulation of a treatment device 20 can result in shortened treatment procedures by reducing the amount of time necessary to effectuate proper position of the treatment device 20. In addition, controlled deflection of the angle at which treatment device 20 exits the underlying endoscope 60 or 120 can reduce internal tissue trauma caused during endoscopic procedures requiring repeated repositioning and manipulation of the entire endoscope. For example, the positioning mechanisms described in FIGS. 3A-15B facilitate the location of treatment instrument 20 within a particular bile duct 200 without repeated manipulation and displacement of the underlying endoscope body. Accordingly, the occurrence of tissue trauma during a treatment procedure can be reduced.

In addition to the positioning mechanisms disclosed above, the system of this application may further include other additional positioning mechanisms, such as those for achieving controlled deflection of the elongated flexible tube of the endoscope.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
    an elongated flexible tube including a distal end and a proximal end, the tube defining a channel extending from the proximal end to an aperture at the distal end;
    a positioning mechanism positionable at the distal end of the flexible tube proximate the aperture, the positioning mechanism configured for movement relative to the distal end of the flexible tube to control a direction at which a treatment instrument extends from the aperture; and
    a control member connected to the positioning mechanism, wherein actuation of the control member controls movement of the positioning mechanism; and
    wherein the positioning mechanism includes an engagement structure, having a first engagement surface and a second engagement surface, the positioning mechanism configured to maintain a releasable engagement between a treatment instrument and the positioning mechanism; and
    wherein the first engagement surface and the second engagement surface are configured to move relative to each other along one or more guide posts.

2. The medical device of claim 1, wherein the releasable engagement comprises a friction fit engagement.

3. The medical device of claim 1, wherein the positioning mechanism is configured for lateral deflection relative to the distal end of the flexible tube through rotation about a pin.

4. The medical device of claim 1, wherein the engagement structure includes a material having a higher coefficient of sliding friction than the flexible tube.

5. The medical device of claim 1, wherein the first engagement surface and the second engagement surface form a clamping mechanism and are movable relative to each other to define an aperture therebetween for receiving a treatment instrument.

6. The medical device of claim 5, wherein the first and second engagement surfaces are respectively formed in first and second blocks.

7. The medical device of claim 5, wherein a distance between the first and second engagement surfaces is adjustable such that an operator can selectively engage and release a treatment instrument during a medical procedure.

8. The medical device of claim 5, wherein the clamping mechanism is configured for lateral deflection relative to the distal end of the flexible tube through rotation about a pin.

9. A medical device, comprising:
    an elongated tube including a distal end and a proximal end, wherein the tube defines a channel extending from the proximal end to an aperture at the distal end; and
    a positioning mechanism configured for movement relative to the distal end of the tube to control a direction of a treatment instrument extending from the aperture, the positioning mechanism including:
        a first engagement structure;
        a second engagement structure, wherein the first engagement structure and the second engagement structure are configured to move relative to each other and relative to the tube to engage and disengage a treatment instrument; and
    a control mechanism coupled to the first engagement structure and configured to control movement between the first engagement structure and the second engagement structure, wherein proximal retraction of the control mechanism is configured to move the first and second engagement structures towards each other;
    wherein the positioning mechanism includes one or more guide posts, wherein the first engagement structure and the second engagement structure are configured to move relative to each other along the one or more guide posts.

10. The medical device of claim 9, wherein the positioning mechanism includes a control mechanism post coupled to the second engagement structure, wherein the control mechanism extends from the first engagement structure, to the control mechanism post, and towards the proximal end of the elongated tube.

11. The medical device of claim 9, wherein an aperture is defined between the first and second engagement structures, wherein a size of the aperture is adjustable upon relative movement between the first and second engagement structures.

12. A medical device, comprising:
    an elongated tube including a distal end and a proximal end, wherein the tube defines a channel extending from the proximal end to an aperture at the distal end; and
    a positioning mechanism configured for movement relative to the distal end of the tube to control a direction of a treatment instrument extending from the aperture, the positioning mechanism including:
        a first engagement structure;
        a second engagement structure, wherein the first engagement structure and the second engagement structure are configured to move relative to each other to engage and disengage a treatment instrument; and
    a control mechanism coupled to the first engagement structure and configured to control movement between the first engagement structure and the second engagement structure; and wherein the positioning mechanism includes one or more guide posts, wherein the first engagement structure and the second engagement structure are configured to move relative to each other along the one or more guide posts.

13. A medical device, comprising:

an elongated flexible tube including a distal end and a proximal end, the tube defining a channel extending from the proximal end to an aperture at the distal end;

a positioning mechanism positionable at the distal end of the flexible tube proximate the aperture, the positioning mechanism configured for movement relative to the distal end of the flexible tube to control a direction at which a treatment instrument extends from the aperture; and wherein the positioning mechanism includes a first engagement structure, a second engagement structure, and one or more guide posts, wherein the first engagement structure and the second engagement structure are configured to move relative to each other to engage and disengage a treatment instrument, wherein the first engagement structure and the second engagement structure are configured to move relative to each other along the one or more guide posts.

* * * * *